(12) United States Patent
Greiner-Perth

(10) Patent No.: US 11,759,797 B2
(45) Date of Patent: Sep. 19, 2023

(54) LIQUID DISPENSER, ESPECIALLY DROPLET DISPENSER

(71) Applicant: Aptar Radolfzell GmbH, Radolfzell (DE)

(72) Inventor: Jürgen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 17/464,070

(22) Filed: Sep. 1, 2021

(65) Prior Publication Data

US 2022/0105524 A1 Apr. 7, 2022

(30) Foreign Application Priority Data

Oct. 2, 2020 (EP) .................................. 20199907

(51) Int. Cl.
*B05B 1/02* (2006.01)
*B05B 1/32* (2006.01)
*B05B 11/00* (2023.01)
*B05B 11/04* (2006.01)

(52) U.S. Cl.
CPC .................. *B05B 1/02* (2013.01); *B05B 1/32* (2013.01); *B05B 11/0037* (2013.01); *B05B 11/047* (2013.01)

(58) Field of Classification Search
CPC ......... B05B 1/02; B05B 1/32; B05B 11/0037; B05B 11/047; B65D 47/18; B65D 47/205; B65D 47/2081; B65D 35/46; B65D 41/32; B65D 47/12; B65D 47/2075; B65D 51/1611; A61J 1/1425; A61J 1/1468; A61J 1/145; A61J 1/1412; A61F 9/0008; B01D 53/229; B01D 61/147

See application file for complete search history.

(56) References Cited

U.S. PATENT DOCUMENTS 8,454,828 B2 * 6/2013 Wochele ............. B05B 11/0067
222/189.09
8,863,998 B2 10/2014 Painchaud et al.
10,538,369 B2 1/2020 Ritsche
10,829,276 B2 11/2020 Höhm et al.
(Continued)

FOREIGN PATENT DOCUMENTS

DE 202012012770 U1 12/2013
DE 102018124067 A1 4/2020
WO 2018141350 A1 8/2018

OTHER PUBLICATIONS

European Search Report issued in corresponding European Application No. 20199907.5, with English translation of category of cited documents dated Apr. 13, 2021 (9 pages).

*Primary Examiner* — Vishal Pancholi
*Assistant Examiner* — Robert K Nichols, II
(74) *Attorney, Agent, or Firm* — FLYNN THIEL, P.C.

(57) ABSTRACT

A liquid dispenser having a liquid reservoir and a discharge head secured thereto, an outlet valve with a pressure chamber and an opposite valve chamber. The liquid reservoir and the valve chamber are each connected at least in phases to a surrounding atmosphere by a ventilation channel. The two channels provided for this purpose, the reservoir ventilation channel and the valve ventilation channel, are separate channels with separate inlets on an outer face of the discharge head.

12 Claims, 3 Drawing Sheets

(56) References Cited

U.S. PATENT DOCUMENTS

2010/0096416 A1* 4/2010 Painchaud ......... B65D 47/2081
       222/496
2011/0155770 A1  6/2011 Painchaud et al.
2020/0055644 A1* 2/2020 Höhm ................ B65D 47/2056
2022/0192872 A1* 6/2022 Greiner-Perth ....... A61F 9/0008

* cited by examiner

LIQUID DISPENSER, ESPECIALLY DROPLET DISPENSER

CROSS-REFERENCE TO RELATED APPLICATION

This claims priority from European Application No. 20199907.5, filed Oct. 2, 2020, the disclosure of which is hereby incorporated by reference in its entirety.

Area of Application and Prior Art

The invention relates to a liquid dispenser, especially in the form of a droplet dispenser. A liquid dispenser of the invention finds use especially for delivery of pharmaceutical liquids. Configured as a droplet dispenser, a liquid dispenser of the invention may especially be used for ophthalmic application of pharmaceutical liquids.

A liquid dispenser of the generic type has a liquid reservoir and a discharge head secured thereto. The discharge head of the generic type comprises a discharge opening and an outlet valve upstream of the discharge opening, which opens as a result of liquid pressure in a pressure chamber with displacement of a valve body, such that liquid can exit through the discharge opening. On opening, the valve body reduces the size of a valve chamber disposed opposite the pressure chamber. In a liquid dispenser of the generic type, the liquid reservoir is at least temporarily connected to a surrounding atmosphere for the purpose of pressure equalization. It has a reservoir ventilation channel in order especially to permit the replenishment of air in the liquid reservoir after the liquid discharge.

According to its configuration, the valve is designed to open at only a low positive pressure in the pressure chamber. Especially in the case of droplet dispensers, it is necessary to permit an exactly dosed discharge of liquid. This is promoted by an outlet valve that opens at a low positive pressure.

Object and Achievement

It is an object of the invention to develop a dispenser of the generic type such that the opening characteristics of the outlet valve that opens at comparatively low positive pressure have better adjustability.

According to the invention, a liquid reservoir is provided for the purpose, which, in the manner already described, has a liquid reservoir and a discharge head secured to the liquid reservoir. The liquid reservoir is preferably formed by a bottle body made of plastic, especially in the form of a compressible squeeze bottle. The discharge head may be connected to the bottle body in one-piece fashion. However, it is preferably connected to the bottle body by a snap or screw connection.

The discharge head has a discharge opening connected to the liquid reservoir via a discharge channel. The outlet valve is provided in the discharge channel. This has a valve body displaceable as a whole with respect to the discharge opening by deformation or displacement, in order to open and close it. The valve body is disposed between the pressure chamber, which is part of the discharge channel, and the valve chamber. When pressurized, the valve body is displaced at least partly in the direction of the valve chamber and reduces the size thereof. If the positive pressure is removed, the valve body returns to its default position that closes the discharge opening, preferably as a result of an elastic reset of the valve body or as a result of application of force by a separate return spring. More particularly, the return spring may be one disposed in the valve chamber mentioned.

The discharge head of the invention has two channels, both of which serve for pressure equalization. The reservoir ventilation channel is provided for the purpose of pressure equalization in the liquid reservoir, and a valve ventilation channel is provided for the purpose of pressure equalization in the valve chamber. The two channels are formed separately from one another. They accordingly have separate inlets provided on an outer face of the discharge head.

This complete separation of the two ventilation channels prevents unwanted effects resulting from the pressure conditions in the valve chamber on the one hand and in the liquid reservoir on the other hand. This prevents, for example, the positive pressure in the liquid reservoir from lowering the tendency of the outlet valve to open during the discharge and/or a reduced pressure that still exists after the discharge in the liquid reservoir from unintentionally favouring the tendency of the valve to open.

The discharge head preferably has an inner component and an outer component which is pushed onto the inner component in an assembly direction and is preferably snap-fitted in situ. The inner component and outer component may collectively have an accommodation space for the valve body, in which case the valve chamber is preferably formed between the valve body and the inner component, and the pressure chamber between the valve body and the outer component.

The reservoir ventilation channel and the valve ventilation channel preferably extend through the inner component and the outer component.

The outer component is preferably penetrated by both inlets. The inner component preferably has two openings on its outside that are in communicating connection with the inlets in the outer component. It may especially be the case here that one of the two channels has, or both channels have, a channel subsection in the form of a ring section-shaped channel subsection between the outer component and the inner component. Such a channel subsection can facilitate the assembly of the inner component and outer component since it permits a more variable relative arrangement of the components.

The inlets of the two channels on the outside of the outer component can be differently aligned relative to one another. They may have a corresponding or adjacent position based on the circumference, i.e. be provided on the same side of the outer component. This facilitates the production of the outer component as an injection moulding since only one common gate in the mould is required for both inlets.

The two inlets are preferably in an offset arrangement in assembly direction of the components. Such an offset arrangement enables an arrangement of the respective channel sections in the inner component which is likewise offset in assembly direction.

The channel sections of the reservoir ventilation channel and of the valve ventilation channel in the inner component preferably each have linear channel subsections that penetrate the inner component and open out at its outer face. Based on a plane, the normal vector of which corresponds to a discharge direction and/or the assembly direction, these linear channel subsections are preferably in an angled arrangement with respect to one another or especially in a parallel arrangement spaced apart from one another, in order to be able to provide them separately from one another with little space available within the component.

It may preferably be the case that a circumferential step is provided between the inlets on the outside of the discharge head. This step may be matched to a protective cap of the liquid reservoir in such a way that the inside of the protective cap, with the cap in place, tightly adjoins the step and hence separates the inlets from one another.

A removable protective cap which is part of the liquid dispenser and protects the discharge opening when in place is accordingly preferably designed such that, when in place, it isolates the two inlets from one another by adjoining the outer component and especially the step mentioned. More particularly, it may be designed such that, when in place, it isolates at least one of the inlets, and preferably both outlets separately, from a surrounding atmosphere. The isolation of the inlets from one another with the protective cap in place prevents any mutual influence between the pressure in the liquid reservoir and in the valve chamber with the protective cap in place.

As already elucidated, the liquid reservoir may especially take the form of a droplet dispenser and may preferably be filled with a pharmaceutical liquid for ophthalmic application.

In the configuration as a droplet dispenser, the liquid reservoir preferably has a means of droplet formation in the region of the discharge opening. This may be a funnel-shaped structure that opens out in the downstream direction. However, the means of droplet formation preferably comprises a droplet formation surface that surrounds the outside of the discharge opening and is at least essentially flat. The droplet formation surface is preferably surrounded on the outside by a break-off edge.

In a liquid reservoir of the invention, especially configured as a droplet dispenser, the valve body may have a closure pin and a pressurization collar surrounding the closure pin. The pressurization area is preferably comparatively large, in order to bring about displacement of the closure pin at low pressure.

It is especially advantageous when the valve body is designed to be internally deformable in an outer region and/or in the region of this pressurization area and is elastically deformed under the action of the liquid pressure. In the case of such a configuration, the outer region is fixed, especially to the inner component, for example by circumferential fixing in a groove in the inner component.

The reservoir ventilation channel may be a connecting channel between an outside environment and the interior of the liquid reservoir which is always open with the cap removed, preferably with provision of at least one filter that frees the incoming air of impurities before it comes into contact with the liquid. In a more complex design, a valve that opens only under reduced pressure in the liquid reservoir may be provided.

For the purpose of discharging liquid, liquid is pressurized upstream of the outlet valve, such that the outlet valve is opened and liquid is discharged. The invention is not limited to any particular pressurization technique. However, in a particularly preferred configuration, the liquid dispenser takes the form of a squeeze bottle dispenser. In such a case, it has a manually elastically deformable bottle body which is squeezed for the purpose of pressurizing the liquid.

The liquid reservoir preferably has an internal volume of less than 250 ml, especially 100 ml, preferably less than 50 ml.

BRIEF DESCRIPTION OF THE DRAWINGS

Further advantages and aspects of the invention are apparent from the claims and from the description that follows of a preferred working example of the invention, which is elucidated hereinafter with reference to the figures.

DETAILED DESCRIPTION OF THE WORKING EXAMPLES

Figure 1:
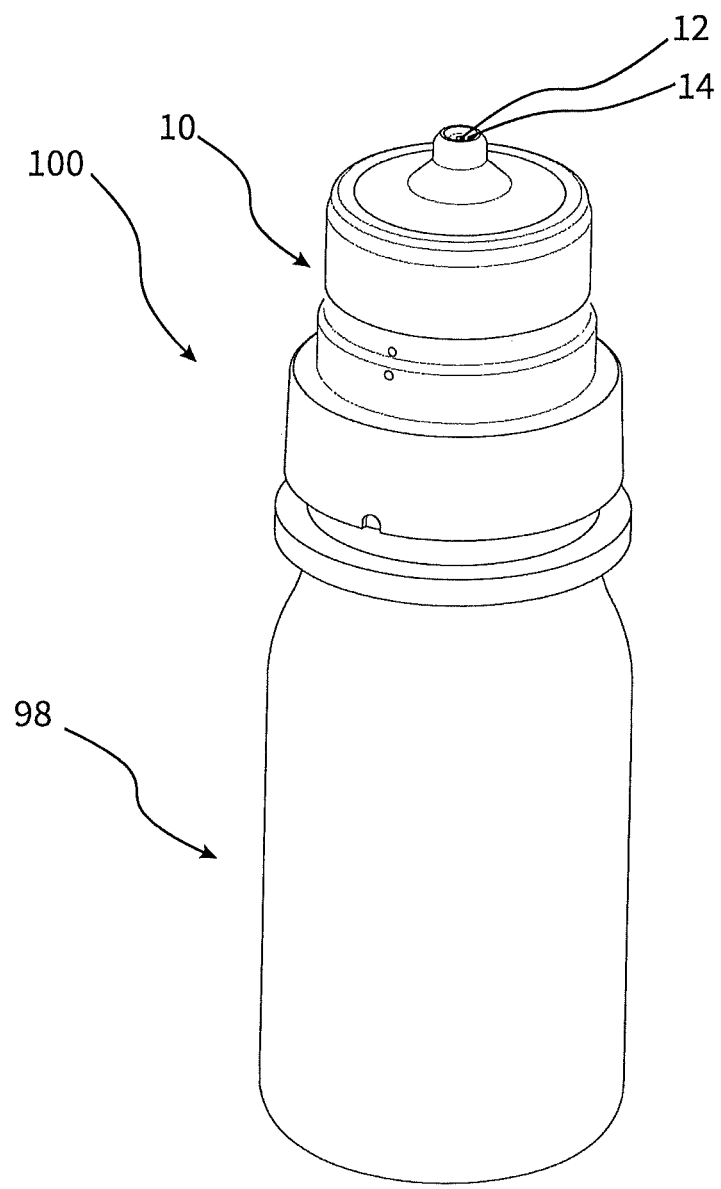
FIG. 1 shows an overall view of a liquid dispenser of the invention without the cap in place.

FIG. 1 shows an illustrative overall view of a liquid dispenser 100 of the invention, but without a protective cap 120.

The liquid dispenser 100 has a bottle body 98 made of plastic which is elastically deformable with a low level of force, called a squeeze bottle. A discharge head 10 is secured to the neck of the bottle body 98, in the present case by means of a snap connection.

The discharge head 10 has a discharge opening 12. Since the illustrative liquid dispenser takes the form of a droplet dispenser, a means of droplet formation is provided in the region of the discharge opening, in the present case in the form of a droplet formation surface 14 which surrounds the discharge opening 12 and is bounded by a circumferential break-off edge.

The dispenser is intended for use in an upturned position in which the discharge opening 12 points downward. In this position, the bottle body 98 is squeezed manually. The effect of this is that an outlet valve 20 in the discharge head 10 opens under the influence of the elevated liquid pressure in the liquid reservoir and allows liquid to arrive at the droplet formation surface 14 in a dosed manner. The liquid collects there until the desired droplet volume has been attained and the droplet becomes detached from the droplet formation surface.

Figure 2:
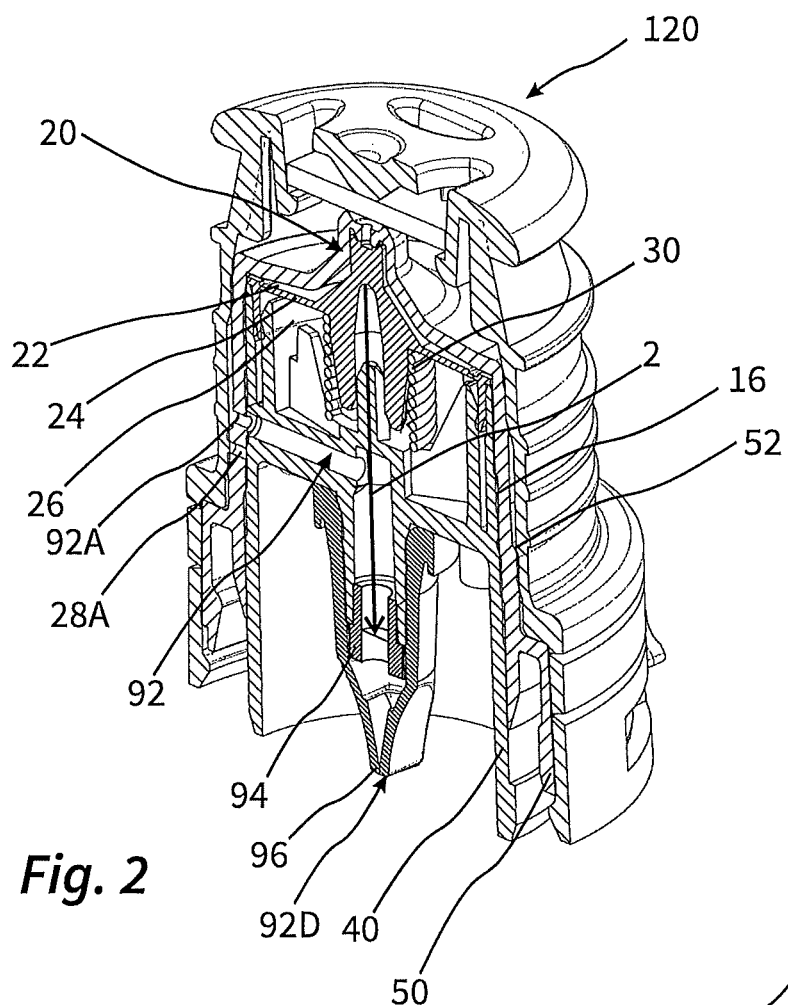
FIG. 2 shows the discharge head of the liquid dispenser in a perspective cross section view.

FIG. 2 shows the discharge head 10 in a perspective cross section view with the protective cap 120 in place. The main components of the discharge head 10 are an inner component 40 and the outer component 50 pushed onto the inner component in an assembly direction 2.

A valve body 24 manufactured from elastic plastic is provided between the two components 40, 50. This valve body has a central closure pin 24A which, in the closed state of the outlet valve, adjoins an inner wall of the outer component 50 surrounding the outlet opening 12. The closure pin 24A merges into a pressurization collar 24B that surrounds the valve pin in a disc-shaped manner. At the outer edge thereof, a securing land 24C is provided, inserted circumferentially into a securing groove of the inner component 40.

In the region of the pressurization collar 24B, a pressure chamber 22 is formed between the valve body 24 and the outer component 50. This is fed with liquid via a discharge channel 16 that extends from an inlet (not shown) at the side of the liquid reservoir 90 via an annular space between the inner component 40 and the outer component 50 into the pressure chamber 22. On the side of the valve body 24 remote from the pressure chamber 22, a valve chamber 26 is provided, in which a return spring 30 that subjects the valve body 24 to a force in the direction of its closure position is provided.

If there is an increase in the liquid pressure in the liquid reservoir 90, there will also be an increase in the pressure in the pressure chamber 22, and the valve body 24 will be displaced downward under deformation in the region of the pressurization collar 24B. This reduces the volume of the valve chamber 26.

Both the liquid reservoir 90 and the valve chamber 26 are connected to a surrounding atmosphere at least in phases in order to achieve pressure equalization. In the case of the liquid reservoir 98, the reservoir ventilation channel 92 provided for the purpose primarily serves the purpose of permitting the inflow of further air if liquid has been discharged beforehand. In the case of the valve chamber 26, the valve ventilation channel 28 serves the purpose of preventing a pressure at variance from ambient pressure from existing over a prolonged period of time in the valve chamber 26 since this could alter the opening characteristics of the outlet valve 20.

According to the invention, the two ventilation channels 28, 92 are separate from one another. Beyond the discharge channel 16, there is accordingly no further functional coupling, as a result of the design of the discharge head, between the respective pressures in the ventilation channels 28, 92. If, for example, there is a reduced pressure in the liquid reservoir 90 since liquid has been discharged beforehand, this does not result in a reduced pressure in the valve chamber 26.

Figure 3:
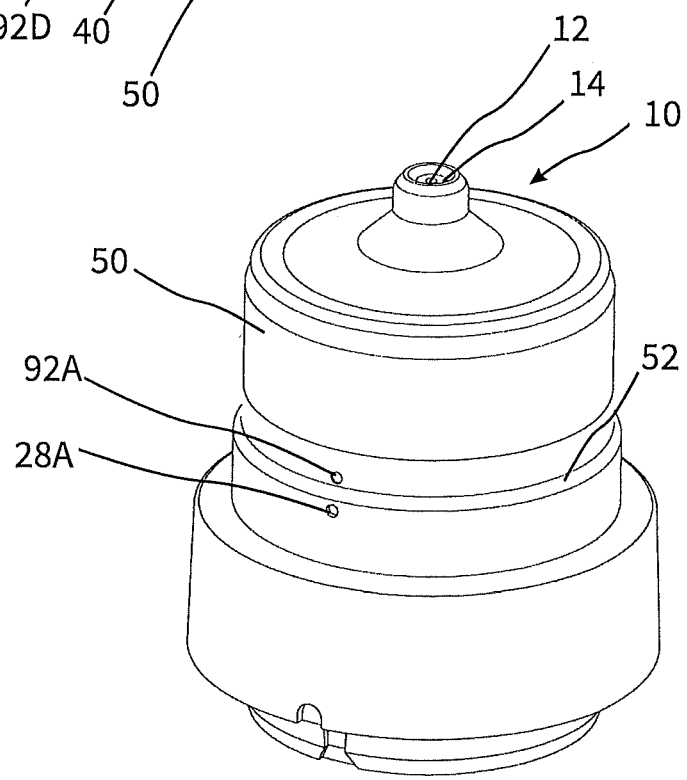
FIG. 3 shows the discharge head in a perspective non-sectional view.

The two ventilation channels 28, 92 each have inlets 28A, 92A on the outside of the outer component 50. This is illustrated by FIG. 3. In this configuration, the two inlets 28A, 92A are provided on the same side of the discharge head 10 but offset from one another in assembly direction 2. This arrangement on the same side permits the utilization of a comparatively simple mould since the inlets 28A, 92A may be produced by means of a common gate in the mould. However, other configurations are also possible and may be viable in particular cases, especially an arrangement of the inlets 28A, 92A on opposite sides.

A step 52 at which the external diameter of the outer component 50 is reduced is provided between the inlets 28A, 92A. This step is advantageous in its interaction with the protective cap 120. As can be seen from FIG. 2, the inside of the protective cap 120, when in place, adjoins the step 52 around the circumference, such that it isolates the two inlets 28A, 92A from one another.

The effect of this isolation by the protective cap 120 is that, even with the protective cap 120 in place, the liquid reservoir 90 and the valve chamber 26 are isolated from one another. Thus, if the cap is placed on immediately after use and with consequent reduced pressure in the liquid reservoir 90 before the pressure in the liquid reservoir 90 is balanced out, the reduced pressure that exists in the liquid reservoir 90 and in the ventilation channel 92 cannot have any effect on the behaviour of the outlet valve. This prevents unwanted emptying of the dispenser, for example in luggage.

Figure 4:
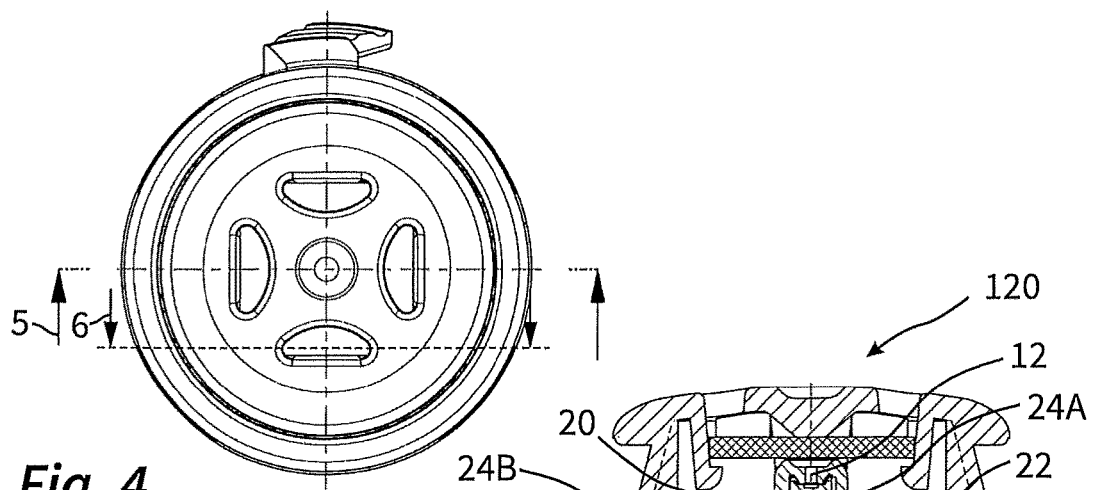
Figure 5:
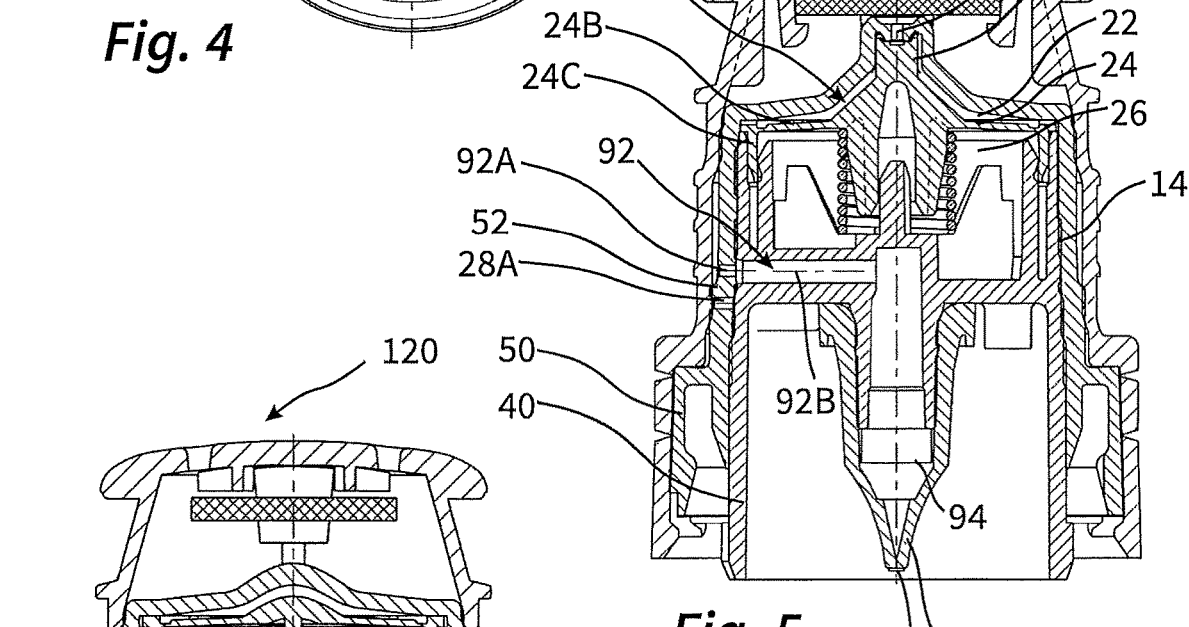
FIGS. 5 and 6 show two cross-sectional planes of the discharge head, the respective plane of intersection of which is illustrated by FIG. 4.
Figure 6:
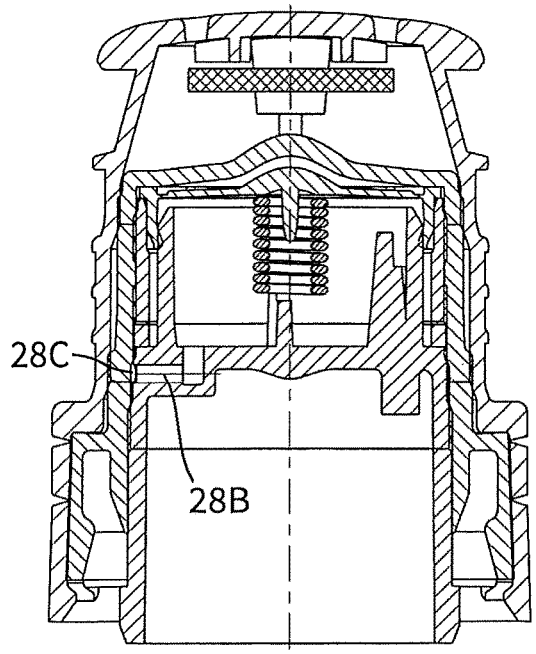

The course of the ventilation channels 28, 92 is/illustrated by FIGS. 4 to 6. FIG. 4 shows the discharge head 10 of the dispenser 100 of the invention from the top. Reference numerals 5 and 6 identify two section planes, the cross-sectional diagrams of which are shown in FIGS. 5 and 6.

Section plane 5 runs through a centre axis of the dispenser and its central discharge opening. The radial channel subsection 92B of the reservoir ventilation channel 92 runs in this plane. Section plane 6 is shifted outward, parallel thereto. A radial channel subsection 28b of the valve ventilation channel 28 runs in this plane.

With reference to FIG. 6, the course of the valve ventilation channel 28 is elucidated in detail first of all. Proceeding from the valve chamber 26, the valve ventilation channel 28 has a short subsection that runs parallel to the assembly direction 2. This is followed by the linear channel subsection 28B mentioned, which penetrates an outer face of the inner component 40. On account of its eccentric arrangement which is not exactly radial, this channel subsection 28B does not open perpendicularly onto the outer face. A channel subsection 28C that adjoins channel subsection 28B is formed by a channel subsection 28C in the form of a ring section that extends around the circumference between the inner component 40 and the outer component 50, preferably running at an angle of around 30°, up to the inlet 28A provided in the outer component 50.

The reservoir ventilation channel 92, which is readily apparent in FIG. 5, extends from the inlet 92A that penetrates the outer component 50 into a radial channel section 92B which is flush with the inlet 92A in the position of relative rotation of outer component 50 and inner component 40 that is shown here. However, it would also be possible for the outer component 50 and the inner component 40 to be connected in a different position of relative rotation, so as to result, between the inlet 92A and the channel subsection 92B in the inner component 40, as already described for the valve ventilation channel, in a channel subsection in the form of a ring section between the inner component 40 and the outer component 50.

On the inside, the radial channel subsection 92B is followed by an axial channel subsection formed partly by a valve body 96 that forms the outlet 92D of the reservoir ventilation channel 92. In addition, a filter unit 94 may be provided here in order to free the incoming air from impurities.

As apparent from the parallel section planes 5, 6 and the ventilation channels 92, 28 arranged therein, the ventilation channels are arranged parallel to one another, but offset from one another with respect to the plane shown in FIG. 4. This means that it is necessary for the inner component 40 to have just one gate for formation of the channel subsections 92B, 28B and that the latter nevertheless can be spaced apart from one another, such that the respective channels have sufficient build space in the inner component.

The invention claimed is:
1. A liquid dispenser comprising:
a liquid reservoir;
a discharge head which is secured to the liquid reservoir and has a discharge opening connected to the liquid reservoir via a discharge channel;
the discharge head having, in the discharge channel, an outlet valve which has a valve body adjoining a pressure chamber and which is at least partially displaceable by liquid pressure in the pressure chamber for the purpose of opening the discharge opening;
the outlet valve having a valve chamber which, based on the valve body, is disposed opposite the pressure chamber;
a reservoir ventilation channel for pressure equalization in the liquid reservoir; and
a valve ventilation channel for pressure equalization between the valve chamber and an external environment;
the reservoir ventilation channel and the valve ventilation channel having separate inlets on an outer face of the discharge head;

the discharge head having an inner component and an outer component, wherein the outer component has been pushed onto the inner component in an assembly direction; and the reservoir ventilation channel and the valve ventilation channel each extending through the inner component and the outer component.

2. The liquid dispenser according to claim 1, wherein: the reservoir ventilation channel and/or the valve ventilation channel having a channel subsection in the form of a ring section-shaped channel subsection between the outer component and the inner component.

3. The liquid dispenser according to claim 1, wherein: the inlets are provided on a lateral outer face of the discharge head, the inlets are offset relative to one another based on the assembly direction, and a circumferential step is provided on the outer face of the discharge head between the inlets.

4. The liquid dispenser according to claim 1, wherein: the discharge head has a removable protective cap that protects the discharge opening when in place; and the protective cap, when in place, isolates at least one of the inlets from a surrounding atmosphere.

5. The liquid dispenser according to claim 4, wherein: the protective cap, when in place, isolates the two inlets from one another and each from the surrounding atmosphere.

6. The liquid dispenser according to claim 1, wherein: the reservoir ventilation channel has at least one filter and/or one inlet valve between an inlet on the outside and an outlet on the reservoir side.

7. The liquid dispenser according to claim 1, wherein: the liquid dispenser is designed as a squeeze bottle dispenser and has a bottle body which is manually elastically deformable for the purpose of pressurization and surrounds the liquid reservoir.

8. The liquid dispenser according to claim 1, further including:
a return spring for the valve body disposed in the valve chamber.

9. A liquid dispenser comprising:
a liquid reservoir;
a discharge head which is secured to the liquid reservoir and has a discharge opening connected to the liquid reservoir via a discharge channel;
the discharge head having, in the discharge channel, an outlet valve which has a valve body adjoining a pressure chamber and which is at least partially displaceable by liquid pressure in the pressure chamber for the purpose of opening the discharge opening;
the outlet valve having a valve chamber which, based on the valve body, is disposed opposite the pressure chamber;
a reservoir ventilation channel for pressure equalization in the liquid reservoir; and
a valve ventilation channel for pressure equalization between the valve chamber and an external environment;
the reservoir ventilation channel and the valve ventilation channel having separate inlets on an outer face of the discharge head;
the liquid dispenser being designed as a droplet dispenser and has means for droplet formation in the region of the discharge opening;
the valve body has a closure pin and a pressurization collar surrounding the closure pin;
wherein the discharge opening is provided in an outer component, and, in the closed state, the closure pin adjoins an inner wall of the outer component surrounding the discharge opening for closing the discharge opening.

10. The liquid dispenser according to claim 9, wherein: the means for droplet formation comprise a droplet formation surface that surrounds the outside of the discharge opening.

11. The liquid dispenser according to claim 9, wherein the pressurization collar is internally deformable and is secured on its outside to the droplet dispenser.

12. The liquid dispenser according to claim 11, wherein the pressurization collar is secured to an inner component of the droplet dispenser.

* * * * *